United States Patent [19]
Gaddini

[11] Patent Number: 6,139,857
[45] Date of Patent: Oct. 31, 2000

[54] METHOD OF REPELLING RODENTS AND VERMIN

[76] Inventor: Norman Gaddini, 1060 Jonive Rd., Sebastopol, Calif. 95472

[21] Appl. No.: 09/456,032

[22] Filed: Dec. 3, 1999

Related U.S. Application Data

[60] Provisional application No. 60/143,326, Jul. 12, 1999.
[51] Int. Cl.⁷ .................................................. A01N 25/00
[52] U.S. Cl. .......................... 424/405; 424/703; 424/705
[58] Field of Search ................................ 424/195.1, 408, 424/457, 703, 405, 601, 705; 222/85, 325

[56] References Cited

U.S. PATENT DOCUMENTS

| | | | |
|---|---|---|---|
| 631,738 | 8/1899 | Dowie et al. ........................... | 424/601 |
| 4,256,241 | 3/1981 | Mesic ....................................... | 222/85 |
| 4,795,637 | 1/1989 | Harding, Jr. ........................... | 424/195.1 |
| 5,039,524 | 8/1991 | Oishi et al. ............................. | 424/408 |
| 5,756,100 | 5/1998 | Martinez ................................ | 424/195.1 |

*Primary Examiner*—Jon P. Weber
*Assistant Examiner*—Patricia D Patten
*Attorney, Agent, or Firm*—Johnson & Stainbrook, LLP; Craig M. Stainbrook; Larry D. Johnson

[57] ABSTRACT

A method of repelling rodents and vermin comprising the steps of providing an effective quantity of dry dusting sulfur and inserting said dusting sulfur into burrowing holes and other spaces traveled by rodents and vermin. The method is primarily directed to gardens and yards where animal burrows are evident, but will work in agricultural fields and living structures as well. In the latter application, the dusting sulfur may be applied, for example, in pipes, underneath floor boards, and inside wall and crawl spaces.

7 Claims, 1 Drawing Sheet

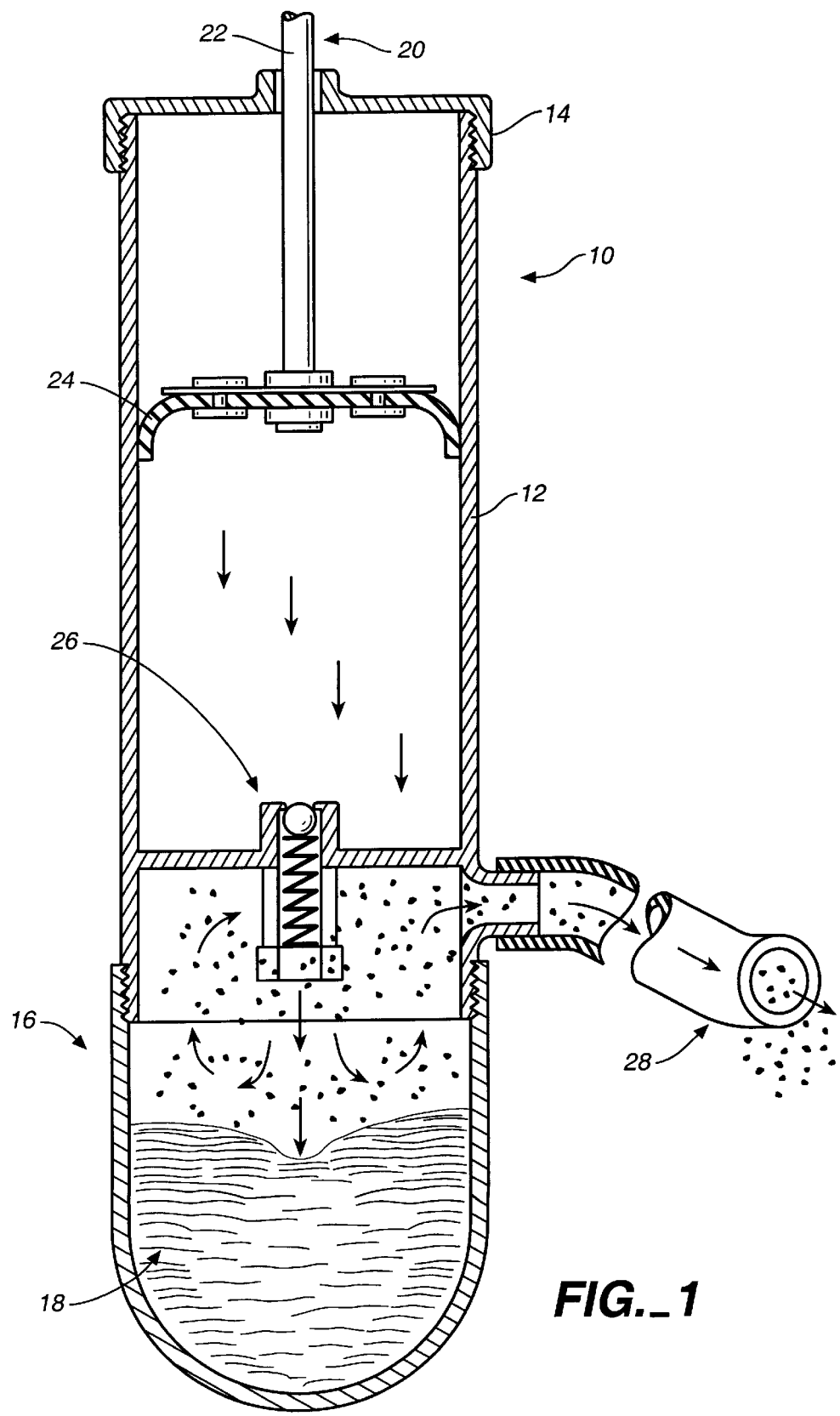
FIG._1

METHOD OF REPELLING RODENTS AND VERMIN

This Appln claims the benefit of U.S. Provisional No. 60/143,326 filed Jul. 12, 1999.

BACKGROUND OF THE INVENTION

1. Field of the Invention

The present invention relates generally to methods for repelling rodents, and more particularly to a method for repelling rodents and vermin from structures, yards, gardens, and agricultural fields areas using dry dusting sulfur irritate the mucous membranes of such pests.

2. Description of the Prior Art

It is well known in the art to repel residential pests and vermin on the one hand, and garden and crop damaging rodents and birds on the other, through the application of chemicals to the area being protected. The prior art includes some repellents in powdered form. However, the various application methods, particularly in the garden and field setting, typically employ aqueous solutions of repellent and further depend upon mixing the repellent in soil or applying the repellent to crops or structures that the pest will taste or smell. Most notably, prior art repellents depend upon an extremely foul smell and taste. Such repellents are only partly effective. The pest can move about with relative impunity should it merely bypass, and not taste or smell the repellent.

In some applications, powdered repellents can be more effective than aqueous repellents. Prior art powdered repellents include U.S. Pat. No. 4,795,637 by Harding, Jr., which teaches a rodent repellent in powder form comprising thujone oil with a powder that does not atomize readily when agitated. Such powders include lime powder, borax powder, pyrethrum powder, silica gel, sulphur powder, sabadilla, pepper powder, tobacco dust, and other powders within a density range of 0.9 grams/cubic centimeter to 1.0 grams/cubic centimeter and of moderately course particle size.

Another powdered repellent is found in U.S. Pat. No. 4,025,643 by Warner, which discloses a free-flowing rodent repellent in which a rodent repellent effective N,N-dialkylsulfenyl dithiocarbamate is admixed with a chemically inert grinding aid having a density of 5 pounds per cubic foot or less to form a non-caking composition. A solids suspending agent, inert to the N,N-dialkyl-sulfenyl dithiocarbamate, and a wetting agent are admixed with the rodent repellent and the grinding agent to produce a water-dispersible, free-flowing powder.

U.S. Pat. No. 631,738 by Dowie teaches a powdered rat repellent consisting of twenty percent chili pepper, five percent hellebore, eight percent sulphate of lime, eight percent phosphate of lime, fifty-four percent carbonate of lime, and five percent oxide of iron. The hellebore and pepper are mixed with a medium to form a light powder that floats and disburses when disturbed. The powdered composition is intended to be sprinkled on infested premises.

Non-powdered compositions include U.S. Pat. No. 5,879,696 by Blumberg discloses a repellent comprising capsaicin or capsaicin derivative compounds. The "hot" compounds are intended to repel animals having capsaicin sensitive receptors.

U.S. Pat. No. 5,674,496 by Etscorn et al., discloses various methods for extracting the active repellent ingredient from pepper plants, particularly habanero peppers, and for using the extract to treat the objects to be protected.

U.S. Pat. No. 3,941,887 by Hermann et al., teaches a variety of repellent compositions and methods for repelling warm-blooded animals, such as rodents, birds, leporines, and ruminants, comprising N(-alkyl, cycloalkyl, phenoxycarbonyloxyalkyl, phenyl, alkyl-phenoyl and alkyl-chlorophenyl)-dithoibiuret derivatives.

U.S. Pat. No. 4,058,402 by Stansbury et al., teaches a water soluble rodent repellent for coating onto buried objects such as cables. Any water soluble or water dispersible composition can be used, but the preferred embodiment disclosed comprises N,N-dimethylsulfenyl dithiocarbamates combined with dimethylsulfoxide and polyvinylalcohol or with one of dimethylsulfoxide and dimethylformamide, and with a hydroxyalkyl cellulose.

The prior art compositions and methods fail to appreciate the advantages of using simple dry dusting sulfur as an eye and mucous membrane irritant to repel burrowing rodents and other pests. Admittedly, some prior art pest repellents include sulfur as an ingredient among others in compositions. However, such compositions necessarily include other ingredients to enhance or give rise to some desirable repellent property or effect. The present inventor has determined that for purposes of repelling several types of pests, simple dry dusting sulfur, with absolutely no other ingredient whatsoever, gives superior results.

Further deficiencies of prior art repellents include high water solubility, rapid deterioration and decrease of effectiveness, costliness, toxicity to humans, and lethality to rodents (resulting in kills that decay in or near living and work place structures).

SUMMARY OF THE INVENTION

The method of repelling rodents of the present invention comprises providing a repellent effective quantity of dry dusting sulfur and inserting it into conspicuous burrowing animal holes or other spaces traveled by certain vermin and rodents. The method is primarily directed to gardens and yards where animal burrows are evident, for example, gopher and mole holes. However, the present method will also work in agricultural fields and horticultural areas, and it may even be used in human living and work structures to repel vermin. In the latter application, the sulfur may be applied, for example, in pipes, underneath floor boards, and inside wall and crawl spaces.

BRIEF DESCRIPTION OF THE DRAWINGS

FIG. 1 is a side elevation cross sectional view of a method of injecting dry dusting sulfur into burrowing animal holes using a manually powered blower.

DETAILED DESCRIPTION OF A PREFERRED EMBODIMENT

Certain powdered mucous membrane irritants are effective in repelling rodents. Eye irritants, in particular, are especially effective. A number of eye irritants may be employed, including sulfur powder, chili and cayenne powder, and the like. Among these, sulfur, being an element, is particularly durable and long lasting, and the instant invention comprises a method of using only dry dusting sulfur to repel burrowing animals.

Dry dusting sulfur and several other eye irritating powders are easily inserted into burrowing animal holes, or other small spaces traveled by rodents and vermin. Insertion can be accomplished in a number of ways, including manual distribution, hand-powered dusters, manual or powered blowers, and placement of gelatinous capsules. When required in agricultural fields, the powder may be injected mechanically into plowed furrows.

An instrument for injecting dry dusting sulfur into burrowing animals holes is illustrated in FIG. 1, a side elevation cross sectional view of a manually powered dusting sulfur blower 10, comprising a cylindrical hollow canister 12 having a cap portion 14 preferably threadably connected to said cylindrical portion, a removable cup portion 16 in which is contained a quantity of dry dusting sulfur 18, said cup portion preferably being threadably connected to said cylindrical portion, a plunger 20 having a handle 22 and a plunger head 24, the latter slidably engaging the interior walls of said cylindrical portion. The blower further has a ball valve 26 to prevent back flow of sulfur dust when the plunger is depressed, and an outlet hose 28 for insertion into a burrowing animal hole or tunnel.

Dry dusting sulfur can be treated and tailored to be extremely light. When inserted into small air spaces, such as burrows, holes, and wall spaces, it will become airborne and broadly dispersed when agitated or disturbed. Moreover, when used in burrows and holes, the sulfur dust hangs in the available airspace as a virtually unavoidable irritant. After encountering the dust, animals will avoid contact by keeping away at a considerable distance.

In the horticultural and agricultural settings, the powder has a distinct advantage over prior art compositions: it has a low water solubility so that it is not washed away by rain, irrigation and watering.

Accordingly, the method of the present invention comprises the steps of providing a repellent-effective quantity of dry dusting sulfur and inserting the sulfur dust into the space or spaces traveled and inhabited by rodents and other vermin, said insertion being accomplished by any of the means outlined above. When so inserted the sulfur dust is durable and easily and widely broadcast by local activity and disturbances, such as those created by burrowing animal activity.

Other advantages of the present method are numerous. Sulfur powder is environmentally safe, non-toxic to humans, harmless to plants, inexpensive, and long-lasting.

What is claimed is:

1. A method for repelling rodents and vermin comprising the steps of:

providing dry dusting composition consisting essentially of sulfur; and inserting said dry dusting sulfur into burrowing animal holes or other small spaces traveled by rodents and vermin.

2. The method of claim 1 further comprising the step of providing means for inserting said dry dusting sulfur composition into the burrowing animal holes or other small spaces traveled by rodents and vermin.

3. The method of claim 2 wherein said dry dusting sulfur composition is inserted into the burrowing animal holes or other small spaces traveled by rodents by manual distribution.

4. The method of claim 2 wherein said dry dusting sulfur composition is inserted into the burrowing animal holes or other small space traveled by rodents with a hand-powered duster.

5. The method of claim 2 wherein said dry dusting sulfur composition is inserted into the burrowing animal holes or other small spaces traveled by rodents by mechanical injection.

6. A method of repelling rodents from the soil in a selected agricultural area comprising the step of:

inserting dry dusting sulfur into the soil comprising the selected agricultural area to be protected from rodents, said dry dusting sulfur containing and combined with no other ingredients.

7. A method of repelling rodents from the soil in a selected horticultural area comprising the step of:

inserting dry dusting sulfur into the soil comprising the selected horticultural area to be protected rodents, said dry dusting sulfur containing and combined with no other ingredients.

* * * * *